(12) United States Patent
Van Der Tol

(10) Patent No.: US 10,571,458 B2
(45) Date of Patent: *Feb. 25, 2020

(54) METHOD AND DEVICE FOR DETERMINING GREENHOUSE GAS, IN PARTICULAR METHANE, EMITTED BY A RUMINANT, IN PARTICULAR A DAIRY ANIMAL

(71) Applicant: LELY PATENT N.V., Maassluis (NL)

(72) Inventor: Patrick Philip Jacob Van Der Tol, Amersfoort (NL)

(73) Assignee: LELY PATENT N.V., Maassluis (NL)

( * ) Notice: Subject to any disclaimer, the term of this patent is extended or adjusted under 35 U.S.C. 154(b) by 645 days.

This patent is subject to a terminal disclaimer.

(21) Appl. No.: 14/743,631

(22) Filed: Jun. 18, 2015

(65) Prior Publication Data

US 2015/0285783 A1 Oct. 8, 2015

Related U.S. Application Data

(63) Continuation of application No. 13/670,542, filed on Nov. 7, 2012, now Pat. No. 9,164,081, which is a (Continued)

(30) Foreign Application Priority Data

May 7, 2010 (NL) ..................... 1037947

(51) Int. Cl.
*G01N 33/497* (2006.01)
*A01K 29/00* (2006.01)
*A61B 5/097* (2006.01)

(52) U.S. Cl.
CPC ......... *G01N 33/497* (2013.01); *A01K 29/005* (2013.01); *A61B 5/097* (2013.01);
(Continued)

(58) Field of Classification Search
CPC ................. G01N 33/497; G01N 33/4972
(Continued)

(56) References Cited

U.S. PATENT DOCUMENTS 3,686,416 A 8/1972 Myer et al.
5,265,618 A * 11/1993 Zimmerman ........ A01K 29/005
600/531

(Continued)

FOREIGN PATENT DOCUMENTS

DE 19960257 8/2001

OTHER PUBLICATIONS

Adam Anson, "Editorial: Eyes an Ears Alert to Dairy Emissions", The Dairy Site NEwsletter—Aug. 21, 2009; text can be located at: http://www.thebeefsite.com/newsletter/256/thedairysite-newsletter-21-august-2009/.*

(Continued)

*Primary Examiner* — Nimeshkumar D Patel
*Assistant Examiner* — Rodney T Frank
(74) *Attorney, Agent, or Firm* — Oblon, McClelland, Maier & Neustadt, L.L.P.

(57) ABSTRACT

A method and a device for determining the emission of greenhouse gas, in particular methane, by ruminants, in particular dairy animals includes counting eructations ("belches") of the animal. This is done by measuring a signal linked to the eructations, for example sound with a microphone. Given that the methane content of an eructation of this type is more or less constant, the total methane emission can be derived therefrom by counting.

26 Claims, 1 Drawing Sheet

Related U.S. Application Data continuation of application No. PCT/NL2011/000030, filed on Apr. 20, 2011.

(52) U.S. Cl.
CPC ............ *G01N 2033/4975* (2013.01); *G01N 2033/4977* (2013.01); *Y02C 20/20* (2013.01)

(58) Field of Classification Search
USPC .......................................................... 73/23.3
See application file for complete search history.

(56) References Cited

U.S. PATENT DOCUMENTS

| | | |
|---|---|---|
| 7,966,971 B2 | 6/2011 | Zimmerman |
| 9,164,081 B2 * | 10/2015 | Van Der Tol ........ A01K 29/005 |
| 2009/0288606 A1 | 11/2009 | Zimmerman |

OTHER PUBLICATIONS

International Search Report and Written Opinion from PCT/NI2011/000030 dated May 25, 2011.

* cited by examiner

METHOD AND DEVICE FOR DETERMINING GREENHOUSE GAS, IN PARTICULAR METHANE, EMITTED BY A RUMINANT, IN PARTICULAR A DAIRY ANIMAL

CROSS REFERENCE TO RELATED APPLICATIONS

This application is a continuation of U.S. Ser. No. 13/670,542 filed on Nov. 7, 2012, which is a continuation of PCT application number PCT/NL2011/000030 filed on Apr. 20, 2011, which claims priority from Netherlands application number 1037947 filed on May 7, 2010. These applications are hereby incorporated by reference in their entireties.

BACKGROUND OF THE INVENTION

1. Field of the Invention

The present invention relates to a method and device for determining greenhouse gas, in particular methane, emitted by a ruminant, in particular a dairy animal.

2. Description of the Related Art

Greenhouse gases play a part in climate change. Livestock breeding makes a substantial contribution to the emission of greenhouse gases, such as carbon dioxide and in particular methane. The global warming potential of methane is 20 to 25 times greater than that of carbon dioxide. The greatest part of this emission is caused by eructations. An average cow is estimated to emit between 500 and 600 litres of methane per day through belching and exhalation. Methane is produced by ruminants as a by-product of the fermentation of organic mass in the gut. It constitutes a significant loss of energy for the animal, estimated at 2 to 12% of the gross energy intake.

It is desirable to find a simple way to determine, or at least estimate, the emission of greenhouse gas, and in particular methane, in the case of animals.

A method and system for measuring emitted greenhouse gas are known from U.S. Pat. No. 5,265,618. Here, a tube with tracer gas ($SF_6$) is swallowed by the animal, from which tube the tracer gas leaks. Furthermore, a sampling system is fitted to the mouth of the animal, where breath samples are taken via a sampling tube. The emission of the greenhouse gas can be determined by analysing the breath samples, wherein proportions of greenhouse gas and tracer gas in relation to the ambient air are determined.

A disadvantage of the known method and system is that this is very complicated, in that the animal must swallow a tracer gas tube and a gas analysis is then carried out using gas analysis equipment. This makes the known method less suitable for application in the case of entire herds of animals. Furthermore, the global warming potential of the tracer gas ($SF_6$) is again a thousand times greater than that of methane

BRIEF SUMMARY OF THE INVENTION

It is an object of the invention to provide a very simple method and system for determining the emission of greenhouse gas, which is suitable for application in the case of large numbers of animals.

The invention achieves this object with a method for determining greenhouse gas, emitted by a ruminant, comprising measuring of a signal related to eructations of the ruminant, and with a device to perform the same. Use is made here, on the one hand, of the insight that an eructation, or belch, is easily recognisable, and, on the other hand, of the finding that the percentage of methane in the eructation is relatively constant, at around 25 to 35%. It then suffices in the first instance to count the eructations in order to be able to determine the emission of the ruminant. In an initial estimate, the eructations per ruminant will be roughly constant in size. It is assumed here that, with the build-up of a quantity of gas in the gut, the shape and other characteristics of the ruminant, in particular the gut, oesophagus and the like, determine the pressure at which the gas can escape. The associated quantity will then also be roughly constant, although this may vary from animal to animal.

In particular, a number of calibration measurements are then also carried out for each ruminant, for example relating to the total quantity of gas and the average proportion of methane. For example, the pressure in the gut at which the gases will escape via an eructation can be calibrated. A technique can be employed here as already described in "Dietary influences on eructation and related phenomena in cattle", J Dairy Sci 1958 41: 1565-1579, which is hereby incorporated by reference in its entirety. Reference is also made here to the study carried out by the KU Leuven [Catholic University of Leuven], see for example http://www.adinstruments.cominews/230909/Ruminate-On-This—Vet-Students-Learn-About-Cow-Digestive-Physiology-with-PowerLab/corporate/, which is hereby incorporated by reference in its entirety, where the positioning of pressure sensors, or at least muscle activity meters, in the stomach is investigated. If this indicates that the pressure in the case of each eructation is in fact constant, or varies within a certain margin, the measurement with simple counting becomes more reliable, enabling better comparison with emission measurements for other animals.

Given that the effect of methane, derived from the product of gas content and global warming potential, is greater than in the case of other respiratory gases, only methane will in principle be discussed below, although the invention is also applicable in principle to other greenhouse gases.

A significant advantage of the invention is that it is very simple, and, in particular, does not entail the swallowing of parts. In very simple terms, the invention entails the automation of the counting of eructations. A recognition step and a counting step must be carried out for this purpose.

In particular, the method involves determining the duration of each eructation, and adding up the time durations determined for each eructation to give a total time duration. The total emission of greenhouse gas can then be determined more accurately on the basis of the measured time durations, through comparison with an average emission per time duration. Here also, a calibration per ruminant can again deliver even more accurate, animal-specific values.

The number of eructations is preferably counted in a predefined time period. In other words, an eructation frequency is determined, wherein the emission in the same time period is determined from the eructation frequency.

In the method according to the invention, it suffices in principle to determine a relative value, by counting the eructations or the time duration thereof. After all, if changes in the emission occur due to changes in the feed supply, the state of health of the animal, etc., this will be visible in the numbers or the time duration. Nevertheless, it may be advantageous to obtain at least an estimate of the absolute emission. To do this, the method advantageously comprises multiplication of the number of eructations by an emission value indicative of the quantity of greenhouse gas per eructation.

Again, a calibration measurement may increase the accuracy. To do this, the method may, for example, comprise correction of the determined emission through multiplication by a correction factor, chosen from an animal-specific correction value, an historical correction value or a greenhouse gas dependent correction factor. Account can thus be taken of an animal-specific value, e.g. if a ruminant (always) produces a relatively large quantity of methane in the breath, or of an historical correction value, e.g. if the breath composition changes with age or during the course of a season, or if a specific type of greenhouse gas is monitored, such as, for example, carbon dioxide, in addition to methane.

In the method according to the invention, a signal related to eructations of the ruminant is measured, and the number and/or time duration of the eructations is determined from the signal. This can be done in a variety of ways. The signal advantageously comprises a sound signal, measured at a point where it is possible to measure the eructations of the ruminant. In particular, the signal comprises a sound signal from the mouth or throat of the ruminant. Use is made here of the insight that an eructation, or "belch", is audibly readily identifiable and characterizable, in terms of pitch, formant locations and/or timbre, etc. The signal can, for example, be picked up with a microphone, such as a contact microphone fitted to the neck or throat of the ruminant, or a directional microphone directed towards the mouth of the ruminant.

The signal may also comprise a pressure signal of the pressure of gases in the gut of the animal, wherein an eructation is counted if the aforementioned pressure drops within a predefined time to at least a predefined extent. Given that gut gases escape with eructations, the pressure will decrease substantially in a short time. Here, with a calibration measurement or the like, it is in turn possible to determine the limits for defining a signal as an eructation, such as: if the pressure difference between the gut and atmosphere decreases by at least 20% within 3 seconds. These limits are of course animal-dependent, feed-dependent, etc.

The method advantageously comprises filtering of the signal in order to increase the signal quality of the signal. Here, filtering helps, for example, to obtain a better signal-to-noise ratio, or at least to reduce the number of false-positive and/or false-negative signals. In particular, the filtering comprises recording of a concurrent optical image of the ruminant and processing with image processing, thereby determining whether the recorded and processed optical image matches an eructation, and/or an acoustic filtering, wherein a frequency spectrum analysis of the sound must meet predefined, in particular animal-specific, requirements, wherein the requirements more particularly relate to peak frequencies, relationships between peak frequencies, sound level and/or changes in the sound level through time, and/or elimination of measured signals which last for a shorter duration than a minimum time duration.

Here, the recording of an optical image with a camera can serve to assess whether the sound signal is associated with an actual eructation. At any rate, the sound signal is more or less heavily influenced by the mouth being open or closed. If the mouth is open, the sound signal will at any rate have more higher frequencies than if the mouth is closed. If required, and advantageously, one or more calibration measurements can in turn be carried out for the situation with a closed mouth and for the situation with an open mouth, wherein a distinction can even be made between a fully open mouth and a half-open mouth. This can be established more reliably with image recognition through processing of the optical image. Many false-positive signals can be filtered out with a check of this type.

Reliability can also be improved with the aid of an acoustic filtering, by analysing the sound signal on the basis of animal-specific requirements, in particular the typical voice sound or eructation sound of that animal. Use can be made here of occurring peak frequencies, i.e. frequencies with the highest sound level, and/or of relationships between sound levels at specific frequencies. This last aspect can be compared with the timbre. Both peak frequencies and timbre are at least partially determined by the shape of the pharynx, just as with a human voice. Analysis of the sound can then also make a clearer distinction between eructations and other sounds, such as normal lowing or ambient sounds.

In particular, the filtering comprises measurement of the pressure of gases in the gut of the animal, and selection of only those signals wherein the aforementioned pressure drops more or less simultaneously. The dropping of this pressure at any rate indicates a genuine eructation. The measurement of the pressure can, for example, be carried out by means of a swallowed sensor, and may be identical to the method which can be applied in the case of the calibration measurements for gut pressure as already described above. It could be said that, with this filtering, the one, acoustic, signal is filtered with the other, pressure, signal.

The invention also relates to a detection device for determining greenhouse gas, in particular methane, emitted by a ruminant, in particular a dairy animal, comprising a sensor designed to measure a signal related to the eructations of the ruminant, and a control device designed to determine from the signal the number and/or the time duration of the eructations, and designed in particular to carry out a method according to the invention. This device thus comprises a sensor for picking up a signal from which eructations can be determined, and also a control device which is designed to actually carry this out, and then to determine the number and/or the time duration of the eructations. As already mentioned previously, relative measurements of this type are sufficient for many purposes, such as changes through time, or in order to monitor reactions to circumstances such as changes in feed or weather.

In particular, the detection device is designed as a collar. Animal-specific monitoring can thus be simply and reliably carried out in situ, or in the adjacent area, where the eructations are most readily detectable.

In embodiments of the detection device, the sensor comprises a microphone, in particular a contact microphone. A microphone of this type is pre-eminently suitable as a sensor for picking up an eructation signal, although, for example, a sensor which measures a gas emission, in particular if this has a composition which differs from normal breath, may also be suitable. It should be noted that a contact microphone is less sensitive to variations in the sound than a microphone which primarily measures mouth sound.

In embodiments of the detection device, the sensor comprises a directable directional microphone. Here, the directional microphone can, for example, be set up at a point where the animals are virtually certain of spending some time, such as a milking stall in the case of dairy animals, or a feeding station. The animal can then be observed for some time, wherein the directional microphone can also be directed towards the mouth of the animal. Although the animals cannot, or at any rate cannot easily, be monitored for a lengthy period, a great advantage is that only one microphone is required, and that this does not have to be fitted to the animal.

In particular, the detection device comprises a signal filter device actively connected to the sensor, and a control device actively connected to the signal filter device. Here, the signal filter device serves to filter the signal, in particular to filter false-positive and/or false-negative signals from the signal. The signal thus filtered can then be further forwarded to the control device. The control device and the signal filter device can of course also form one unit.

The signal filter device advantageously comprises a frequency analysis device in order to carry out a frequency analysis of a sound signal. The same advantages as in the case of the corresponding method according to the invention also apply here. In particular, typical frequencies or frequency relationships can be determined from a few calibration measurements for an eructation of the animal concerned. These are then programmed into the device, so that the measurements can be carried out more reliably.

BRIEF DESCRIPTION OF THE DRAWINGS

The features and advantages of the invention will be appreciated upon reference to the following drawings, in which.

DESCRIPTION OF ILLUSTRATIVE EMBODIMENTS

Figure 1:
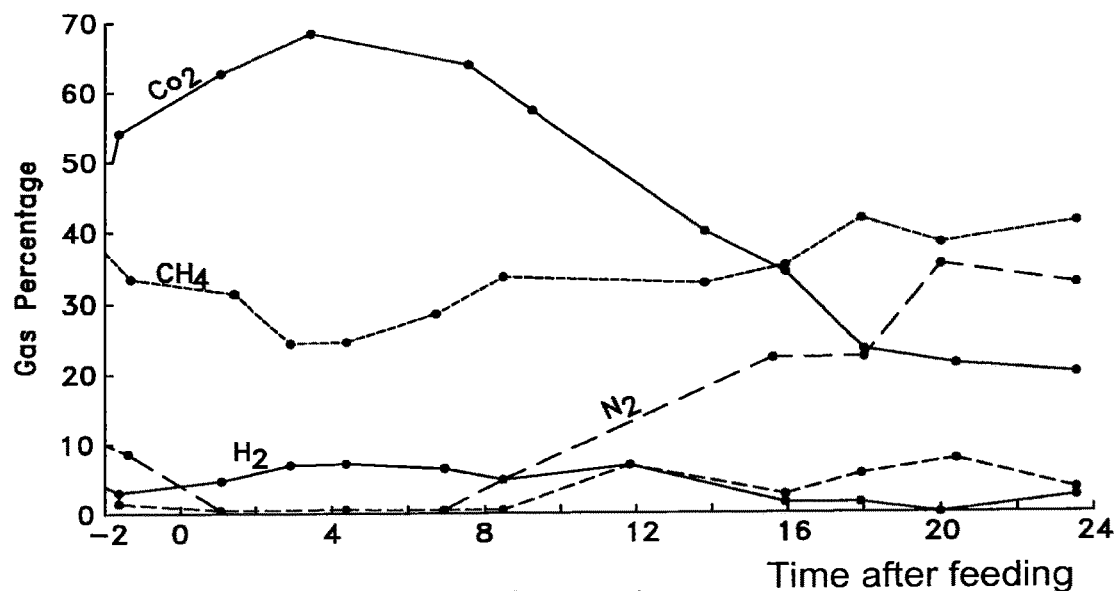
FIG. 1 shows a diagram with the composition of gut gas.

The following is a description of certain embodiments of the invention, given by way of example only and with reference to the drawings. The diagram in FIG. 1 shows the composition of gut gas as a function of time, for a milking cow with a diet of alfalfa, hay and grain. It can be seen that the proportion of methane varies very little, and is continuously around 35±5%. This constancy in composition, which then also applies to the composition of eructated gas, constitutes a basic insight of the invention. It should be noted that the proportion may of course be dependent on the diet, the animal species or the animal race, etc. It can also be clearly seen that the proportion of carbon dioxide varies so substantially through time that a reliable total measurement from simple counting is not possible. Nevertheless, counting of the eructations will always be able to provide an indication of changed circumstances.

Figure 2:
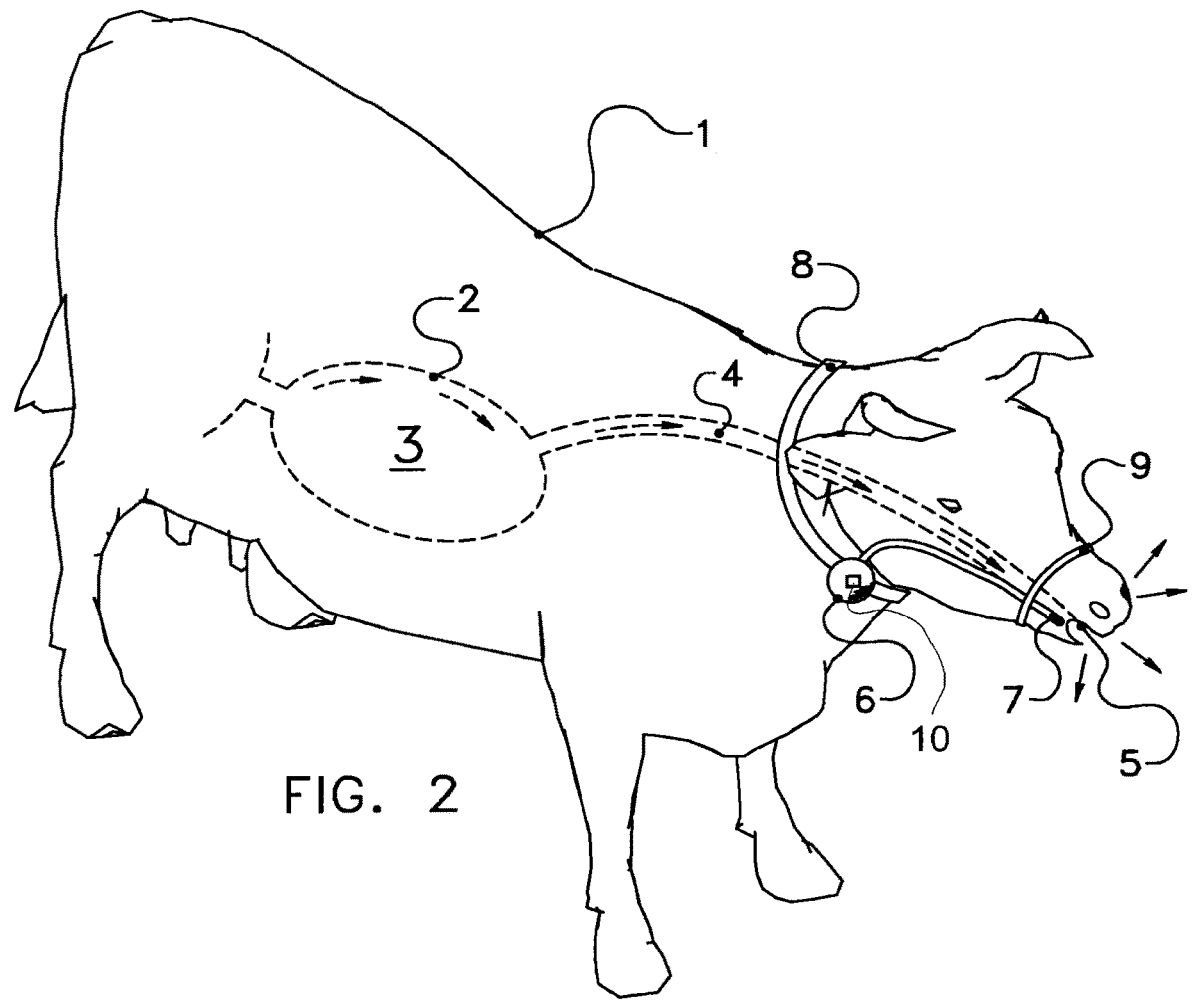
FIG. 2 shows an embodiment of a detection device according to the invention.

FIG. 2 shows schematically a device according to the invention. Here, a cow 1 has a gut 2 with gut gases 3, which are emitted via the oesophagus 4 and the mouth 5 in the direction of the arrows. A measurement and control device 6 with a microphone 7 is hung around the cow with a collar 8 and an ancillary band 9.

The gut gases 3 are a by-product of the digestion through fermentation of organic mass in the gut 2. If the gut gas pressure becomes higher and higher, a limit is reached at a given time, wherein an eructation (belch) will occur, wherein a quantity of gut gas escapes via the oesophagus 4 and the mouth 5. This is accompanied by a measurable sound signal. To measure this signal, a microphone 7 is disposed close to the mouth 5, with an ancillary band 9 for positioning.

This microphone 7 will in principle pick up all sounds which are audible close to the mouth 5. These sounds comprise all eructations, but also feeding and rumination sounds, and also sounds from the environment. A signal filter device 10 is provided in the control device to filter eructations from the total signal. The filtered or unfiltered signal is offered to the control device 6, which counts the eructations, in order to determine the methane emission therefrom. If required, the control device 6 can also determine the duration of each eructation, thereby providing a more accurate total measurement. An even greater accuracy can be achieved with simultaneous recording of an optical image, wherein an eructation must be accompanied by an open mouth.

It should be noted that collars with a built-in microphone are already commercially available. These contact microphones, fitted to the neck/throat of a dairy animal, are able to record sound and determine rumination activity therefrom. A system of this type is, for example, available on the market under the name of Lely Qwes HR. By programming the sound-processing software on the basis of calibration measurements, and possibly a filtering, this apparatus can serve as a device according to the present invention.

Further modifications in addition to those described above may be made to the structures and techniques described herein without departing from the spirit and scope of the invention. Accordingly, although specific embodiments have been described, these are examples only and are not limiting upon the scope of the invention.

What is claimed is:

1. A method for determining greenhouse gas, emitted by a ruminant, comprising:
   measuring of a signal related to eructations of the ruminant;
   determining from the signal at least one of: a number of the eructations and time duration of the eructations,
   wherein the signal comprises a sound signal.

2. The method according to claim 1, wherein the greenhouse gas is methane and wherein the ruminant is a dairy animal.

3. The method according to claim 1, comprising determining the time duration of each eructation, and adding together the time durations determined for each eructation to give a total time duration.

4. The method according to claim 1, comprising multiplying of the number of eructations by an emission value indicative of the quantity of greenhouse gas per eructation.

5. The method according to claim 1, comprising correcting of the determined emission through multiplication by a correction factor, chosen from an animal-specific correction value, an historical correction value or a greenhouse gas dependent correction factor.

6. The method according to claim 1, wherein the sound signal is measured at a point where it is possible to measure eructations of the ruminant.

7. The method according to claim 1, wherein the sound signal is from the mouth or throat of the ruminant.

8. The method according to claim 1, comprising filtering of the signal to increase the quality of the signal, wherein the filtering comprises at least one of:
   recording of a concurrent optical image of the ruminant and processing the concurrent optical image with image processing, thereby establishing whether the recorded and processed optical image matches an eructation;
   an acoustic filtering, wherein a frequency spectrum analysis of the sound must meet predefined animal-specific requirements;
   eliminating of measured signals which last for a shorter duration than a minimum time duration;
   measuring of the pressure of gases in the gut of the animal, and selecting of only those signals wherein the aforementioned pressure drops more or less simultaneously.

9. The method according to claim 8, wherein the predefined requirements relate to at least one of: frequencies, relationships between peak frequencies, a sound level, and changes in the sound level through time.

10. The method according to claim 1, wherein the sound signal is detected by a microphone.

11. The method according to claim 10, wherein the microphone is a contact microphone.

12. The method according to claim 1, wherein the sound signal is detected by a directable directional microphone.

13. A method for determining greenhouse gas, emitted by a ruminant, comprising:
    measuring of a signal related to eructations of the ruminant; and
    determining from the signal at least one of: a number of the eructations and time duration of the eructations,
    wherein the signal comprises a pressure signal of the pressure of gases in the gut of the animal, wherein an eructation is counted if the aforementioned pressure drops within a predefined time to at least a predefined extent.

14. The method according to claim 13, wherein the greenhouse gas is methane and wherein the ruminant is a dairy animal.

15. The method according to claim 13, comprising determining the time duration of each eructation, and adding together the time durations determined for each eructation to give a total time duration.

16. The method according to claim 13, comprising multiplying of the number of eructations by an emission value indicative of the quantity of greenhouse gas per eructation.

17. The method according to claim 13, comprising correcting of the determined emission through multiplication by a correction factor, chosen from an animal-specific correction value, an historical correction value or a greenhouse gas dependent correction factor.

18. The method according to claim 1,
    wherein the determining is performed by a control device and the measuring is performed by a sensor.

19. The method according to claim 18, wherein the sensor comprises a microphone.

20. A method for determining greenhouse gas, emitted by a ruminant, comprising:
    measuring of a signal related to eructations of the ruminant;
    determining from the signal an eructation frequency by counting the number of eructations in a predetermined time period, and
    determining greenhouse gas emission from the eructation frequency.

21. The method according to claim 20, wherein the measuring is performed with a directional microphone set up at a milking stall or a feeding station.

22. The method according to claim 19, wherein the microphone is a directional microphone set up at a milking stall or a feeding station.

23. The method according to claim 5, wherein the measuring is performed with a directional microphone directed towards a mouth of the ruminant.

24. The method according to claim 19, wherein the microphone is a directional microphone directed towards a mouth of the ruminant.

25. The method according to claim 1, further comprising recording an optical image with a camera, and assessing whether the sound signal is associated with an actual eructation.

26. The method according to claim 6, further comprising filtering of the signal, wherein the filtering comprises measurement of a pressure of gases in a gut of the ruminant, and selecting only those signals wherein said pressure drops substantially simultaneously with said sound signal.

* * * * *